US006577397B1

(12) United States Patent
Wadman

(10) Patent No.: US 6,577,397 B1
(45) Date of Patent: Jun. 10, 2003

(54) SCATTEROMETER

(75) Inventor: Sipke Wadman, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/466,409

(22) Filed: Dec. 17, 1999

(30) Foreign Application Priority Data

Dec. 21, 1998 (EP) .............................................. 98204352

(51) Int. Cl.$^7$ ........................ G01N 21/47; G01B 11/30
(52) U.S. Cl. ...................................... 356/446; 356/600
(58) Field of Search ............................... 356/445–448, 356/600

(56) References Cited

U.S. PATENT DOCUMENTS 5,241,369 A    8/1993    McNeil et al. ............... 356/445

FOREIGN PATENT DOCUMENTS

WO    WO9633401    10/1996    .......... G01N/21/57

*Primary Examiner*—Frank G. Font
*Assistant Examiner*—Amanda Merlino

(57) ABSTRACT

A scatterometer for the investigation of surface quality causes a radiation beam (15) with a well-defined direction to fall upon a sample under test (12). The radiation scattered by the sample is intercepted by a screen (10). The two-dimensional image on the screen is captured by a detection system (8). The electric output signal (S) of the detection system is processed for providing a figure of merit of the sample.

7 Claims, 2 Drawing Sheets

SCATTEROMETER

The invention relates to a scatterometer comprising a radiation source for providing a radiation beam and means for guiding the beam towards a sample location. The invention also relates to a method of operating a scatterometer.

Many surfaces of industrial products have a physical structure with certain properties as to enhance the functionality of the product or to improve its appearance. A few typical examples are the extremely smooth surfaces of high quality optical components, wear-resistant layers on cutting tools, the surface of paints, the finely textured plastic parts of surfaces of cosmetics packages and decorative personal care products, the pressing of rolling textures produced in sheet metal, and the high gloss metallic-looking laquers for the automotive industry.

These and many other products are said to have a surface texture. Texture is recognised as the property that determines the human interface, in other words generally how a product feels and looks. The "looks-part" of the texture is called the optical appearance. The optical appearance is a result of what the surface does with light inciding on the surface from the environment. Incident light comes from many directions in many cases and it can be reflected, transmitted, re-emitted, absorbed, coloured, diffused and scattered by surface roughness or structures or by the presence of small particles.

The assessment of textures for optical appearance is usually made in one or more of three methods: visual comparison, gloss and colour measurement, mechanical surface geometry measurement.

Visual assessments are made by visually comparing a product surface to certain standard textured surfaces by trained personnel. Visual appearance is governed by the geometrical outline of the surface and the optical properties of the material itself. Visual texture assessment of e.g. scratches is very difficult with light-coloured surfaces, because there the texture influence is overwhelmed by the strong reflection. White, moderately rough or fine surfaces do not look very different to the eye.

A gloss meter is a simple device that projects a light beam on the surface and measures the intensity ratio of the specular reflected beam and the diffused light in a halo around the specular reflection. This is done under fixed angles of incidence, often 30 or 60 degrees.

Mechanical microgeometrical measurements with contact probes (surface-tests) generate 1-D, 2-D or 3-D maps of the surface. By mathematical evaluation many statistical variants can be obtained by this method, like the well-known roughness measure $R_a$, average slope or peak counts. The method tries to find a relation between the optical appearance of the surface and its geometry.

The latter two methods assay to define certain figures of merit, derived statistically from observational data, that have a relation to the optical appearance.

In general terms, the limitations of these methods originate from the indirectness of the measured parameters. As an example, condensed statistical data derived from a surface measurement comprise a few merit figures that describe the geometrical shape of the surface texture quite well. The proposition is that there exists a relation between the geometrical data and how the surface looks to the eye. The subjective and personal factor makes this relation erratic and irreproducible.

As a second problem, there is the limitation of incomplete data fields. A gloss meter measures optical properties, but does so in a very limited way: only one incidence angle and two (direct and forward scattered) directions of reflection. This does no right to the wealth of variability of surfaces, angles of incidence effects, azimuthal effects, hemispherically strayed light. The optical appearance of a product is determined by the sum of all reflected light (or re-emitted by translucent materials) in the entire hemisphere, originating from incident light from the entire hemispherical environment.

The optical appearance of a textured surface (all surfaces have a texture, natural or purposely added) is formed by light reflected off this surface and entering the eye. Assuming a parallel light beam illuminating a moderately rough surface such as an automobile dashboard, part of the light reflects specularly in a certain direction, but a part also diffuses in other directions. Such a surface is said to be not perfectly diffuse. As seen in FIG. 1, the eye 1 captures light diffused off the product from different parts 3, 4 of the surface 2 under different angles. This light may have different intensities at different angles, so the surface may appear to have different brightness at different parts of the products, e.g. darker at lower angles.

Any light diffused in other directions than captured by the eye is lost to the eye altogether. The same is true for the usual form of gloss meters. If a light beam is aimed at a surface, it is necessary to measure the light diffused in all directions in the upper hemisphere, not integrated but with directional resolution, to fully describe the optical behaviour. To be complete, this should be done for incident light from any direction within the entire hemisphere, i.e. under all vertical (ascension) and horizontal (azimuth) angles. The full image of the directions and intensities of the diffused radiation can be obtained by measuring this hemispherical intensity distribution for multiple combinations of incident height and azimuth. The usual method for such measurements is to scan the entire hemisphere with a scatterometer with a moving detector as known from, inter alia, the German patent application no. 33 12 948. A complete measurement takes many hours in practice.

An object of the invention is to provide a scatterometer that can provide a reliable figure of merit of a surface in a relatively short time.

The object of the invention is achieved, when the scatterometer comprises a screen for intercepting radiation scattered from the sample location, and a radiation-sensitive detection system for capturing a two-dimensional image of the screen and converting it into an electric detector signal. The screen may be used in reflection or transmission and has the usual properties of a projection screen. The two-dimensional image formed on the screen represents the angular distribution of the radiation scattered by a sample arranged at the sample location. The image is therefore a Fourier-like transform of the physical properties of the sample, in which a spatial variation in physical properties of the sample is transformed to an angular variation of radiation energy. The use of an image detector, e.g. a video camera, allows a fast capture of the image, being the full distribution of the scattered radiation.

The screen may be flat, but it is preferably wholly or partly dome-shaped and centred substantially on the sample location, in order to capture all radiation scattered by the sample within an entire hemisphere. The dome itself may also be a hemisphere. The radiation source may be monochromatic, e.g. a semiconductor or other type of laser. For spectral investigations, such as reflection as a function of wavelength and angle of incidence, a polychromatic source, e.g. a white light source, may be used.

The sample at the sample location may be investigated in reflection or in transmission. In the latter case the incident beam and the scattered radiation to be detected are at opposite sides of the sample, and the measurement is indicative not only for the physical properties of the entrance and/or exit surface of the sample but also of its interior. The sample is preferably mounted on an adjustable stage, to allow changes in the azimuth of the sample. The image on the screen is preferably relayed to the detection system by a wide-angle optical system such as a fish-eye lens or a convex mirror which may-have the form of an off-axis mirror arranged close to the sample location.

The objects, advantages and features of the invention will be apparent from the following more particular description of preferred embodiments of the invention, as illustrated in the accompanying drawings, in which FIG. 1 shows scattering of radiation from a surface;

Figure 1:
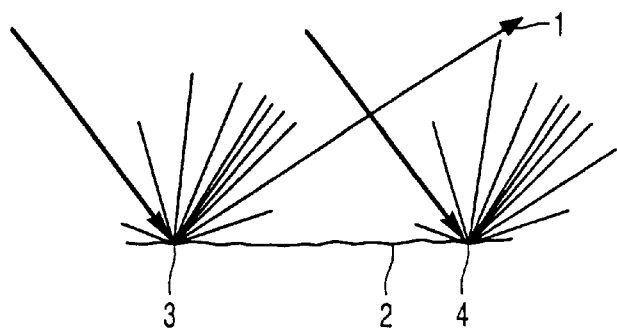
Figure 2:
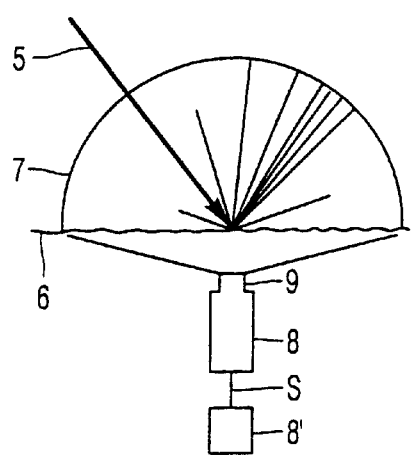
FIG. 2 shows a scatterometer according to the invention.

FIG. 2 shows a scatterometer according to the invention. A beam of radiation 5 is incident on a sample 6, shown as a textured surface. A shallow concave dome 7 intercepts the hemispherical intensity distribution of the radiation scattered by the sample. The inside of the dome is coated with a diffuse coating. The image formed by the scattered radiation on the inside of the dome is a Fourier-like transform of the texture of the surface of sample 6. The image is captured by a video camera 8 using a wide-angle optical system 9. The optical system may also be a reflective system. The camera provides an electric detector signal S representing the captured image. Calculating means 9 process the detector signal to derive one or more figures of merit characterizing the measured sample.

Figure 3:
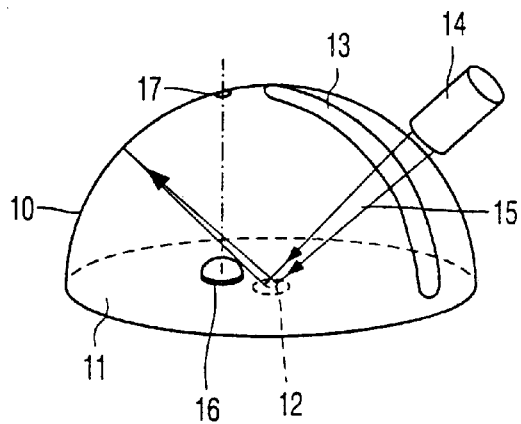
FIG. 3 shows an alternative embodiment of the scatterometer.
Figure 4:
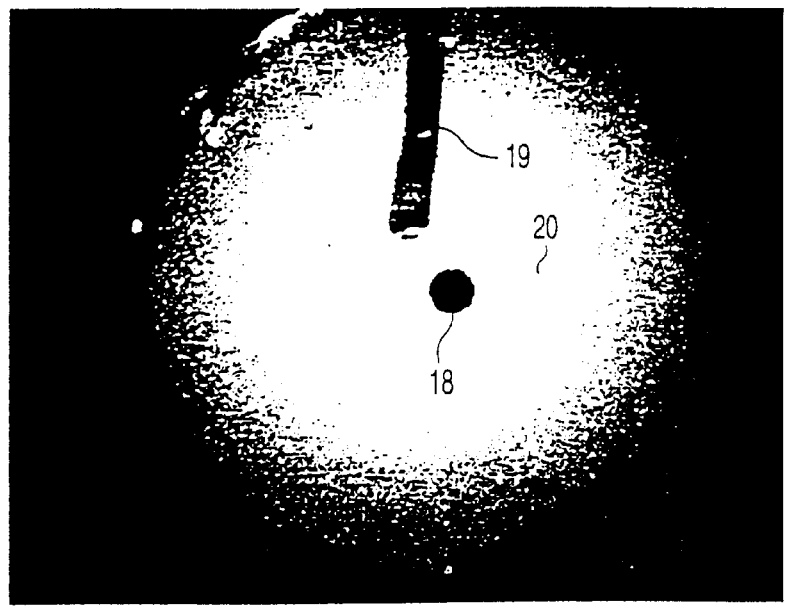
FIG. 4 shows an image of the distribution of the scattered radiation.

In a practical embodiment the dome takes the form of a deep-drawn stainless steel dome 10 as shown in FIG. 3. The dome has a diameter of 22 cm and is coated with a diffuse neutral grey coating. The dome has a base plate 11 which is dull black with a central hole 12 through which a part of the sample surface is visible. The dome has a meridional slot 13 through which a light source 14 projects a light beam 15 on the sample. The light source can be moved to different heights or inclinations with the beam aiming at the sample all the time. The light source may be arranged away from the dome, the radiation beam being guided to the dome by an optical fibre cable. Next to the sample an off-axis convex mirror 16 is placed. Right above this mirror there is a camera port 17 for a video camera to look at the image of the dome surface reflected in the mirror, which is designed to reflect the entire inside of the dome. The illuminated area of the sample can be adjusted by a not-shown diaphragm in the light path from approximately Ø 12 mm to Ø 2 mm. The spot is focussed on the dome and has a diameter of ≈30 mRad. The resolution can be further improved to 1–5 mRad. The reflective wide-angle system 16 in FIG. 3 forms, in general, a deformed image of the inner dome surface. FIG. 4 shows such an image. The central black hole 18 is an image of the camera viewport, the radial black band 19 at the top is an image of a slot through which the incident beam can be aimed at the sample at any angle between +80 degrees (for reflection) and −80 degrees (for translucence). On a preferred embodiment of the screen a, preferably regular, array of dark marks is applied in order to calibrate the image deformation by the optical system. The marks appear in the image as an array of dark spots 20. The spots are useful for subsequent software correction of the image and transformation to a real spherical stereographic projection. The spots need not be used in all measurements, but are useful for calibration measurements. The correction of the deformation may alternatively be calculated by ray-tracing or mathematically if the shapes of the surfaces are known.

Images can be obtained with video frequency, e.g. 25 Hz. There is a provision for continuous adjustment (e.g. 10 values in practice) of incident beam ascension and sample azimuth, so that a complete set of, say, a few hundred images is obtained in a few minutes to form the basis of further data processing.

When using a colour video camera, the same measurement also provides data about the wavelength dependent behaviour of the sample. Colour video uses three wavelength bands, which is not a real colour measurement in the CIE sense, but it brings very useful direction-dependent colour information of the sample. This is of special interest for diffractive surfaces such as holograms.

Normally, the camera is aimed to view the image on the screen, while the sample itself in not visible for the camera. In a special embodiment of the scatterometer there are provisions to allow the sample itself to be imaged directly by the camera. The camera may be aimed at the sample by slightly turning the camera from the mirror to the sample. In this viewing mode the sample may be illuminated by diffuse light obtained through one or more additional lamps that illuminate the inside of the dome. The sample may also be illuminated by a collimated beam of light or by a bright spot projected on the screen. The specular reflection of the beam or spot off the sample may fall in the camera or to the side of the camera, depending on the desired characteristic of the sample to be observed. The viewing mode allows different characteristics of the sample texture to be retrieved, because the sample is viewed directly and not via a Fourier-like transformation.

An increase of the potential of the scatterometer according to the invention comes from data processing. Image processing software may give the required data reduction. A portable computer has sufficient power to process the large amounts of information involved. The information processing may perform the following functions:

1) First the image is captured and stored on an electronic storage medium. For one new, totally unknown texture, typically one hundred images can be captured with different settings for incidence angle of the beam (ascension) and azimuth angle of the measured surface area. For surfaces already partly known, as in the case of comparative measurements of the quality of standard textures, only one or a few images will be needed.

2) The second step is to correct the intensity distribution of the image for the variation in surface intensities due to the known variation of sample-dome distance.

3) The third step is the correction of the distortion of the image caused by the optical system. The result of this step is a stereographic projection centred around the specular reflection angle or centred on the dome apex.

Figure 5:
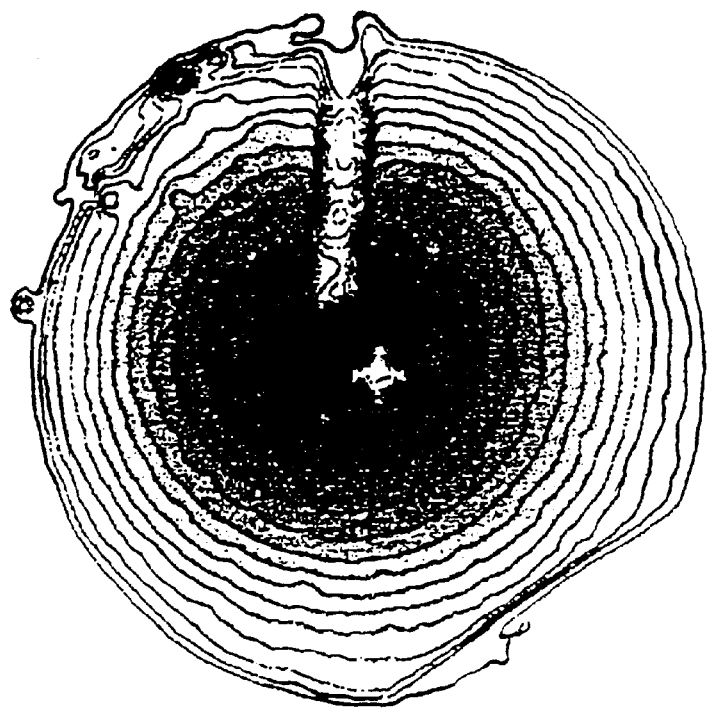
FIG. 5 shows isophotes of the image in FIG. 4.

4) The next step is image processing to reduce the volume of image data. As an example, isophotes can be determined in the image. FIG. 5 shows the 16-levels isophotes image of FIG. 4.

5) The isophote image data is further reduced in the following step by measuring relevant cross-sectional intensity profiles, which in turn form the basis of the calculation of quantitative parameters, such as profile widths at several levels, lateral and sagittal, excentricity, spiking, graininess, steepness of the profiles. These parameters form the input for the calculation of a limited set of figures of merit relevant for the texture under study.

Each type of sample requires its own set of typifying figures of merit. The number of figures of merit is preferably not larger than three or four for reasons of practicality. The scatterometer can perform a complete measurement and calculate the figures of merit for a texture in less than a minute.

Applications for the scatterometer are found in a very wide field of industry, examples of which are the following:

- The optical industry for optical surfaces, coating, reference planes, tools, abrasives
- The machining industry for tribological surfaces, tooling structures, rolling structures
- The polymer-processing industry for the monitoring of wear of insert mould textures, dents and scratches in products, spark erosion-, etch-, powder blasting- and laser textures
- The coating industry for laquers, paints, powder coating, galvanic coatings
- Lighting industry for characterization of reflective and translucent materials
- Ceramic industry for characterization of sintering processes and sintered surfaces
- The printing industry for appearance of decorative printings
- Mining industry for the characterization of minerals
- Automotive industry for coatings, textures, tool wear, materials
- Packaging industry for appearance of "self-selling" packages
- Paper industry for measuring for surface quality
- Cosmetic industry for produce appearance, human skin, packaging
- Designers in all industries get an objective tool for characterising selection textures for products where appearance is important
- Standardisation of textured surfaces.

It was also found that many minerals with glittering, opalescent of other direction-dependent appearance give typical light patterns in the scatterometer. It is clear that such a complicated scatter pattern requires a set of figures of merit quite different from the pattern of metal samples. Examples of figures of merit are:

- The asymmetry of the pattern on the screen, which may be expressed as the ratio of the sagittal FWHM (full-width-half-maximum) intensity over the tangential FWHM intensity.
- The gloss factor, defined as the ratio of the area of the pattern at 20% of its maximum intensity and the area of the pattern at 80% of its maximum intensity.
- The maximum intensity of the pattern.
- The diffracted gloss, suitable for quantifying scratches, which may be determined as the ratio of the maximum intensity with the sample at an azimuth of 0° and the maximum intensity with the sample at an azimuth of 90°.

What is claimed is:

1. A scatterometer comprising:

a radiation source for providing a radiation beam;

means for guiding the radiation beam towards a sample location;

a screen for intercepting radiation scattered from the sample location; and a radiation-sensitive detection system for capturing a two-dimensional image of the screen and converting it into an electric detector signal, wherein the screen includes a meridional slot through which the radiation beam travels.

2. Scatterometer according to claim 1, in which the screen is dome-shaped and centred substantially on the sample location.

3. Scatterometer according to claim 1, in which the direction of the beam at the sample location is adjustable.

4. Scatterometer according to claim 1, in which a convex mirror is arranged between the screen and the detection system.

5. Scatterometer according to claim 1, which is provided with calculating means for deriving a figure of merit of a sample at the sample location.

6. A method for deriving a figure of merit of a sample, comprising the steps of:

irradiating the sample with a radiation beam;

intercepting the radiation scattered by the sample on a screen; and capturing a two-dimensional image from the screen and converting the image into an electric detector signal, wherein an array of marks on the screen is captured and used for correcting a deformation of the image.

7. Method according to claim 6, in which in an additional step a direct image of the sample is captured by the camera.

* * * * *